United States Patent [19]

Peterson

[11] 4,118,591
[45] Oct. 3, 1978

[54] 3,7-INTER-M-PHENYLENE-4,5,6-TRINOR-PGD₁ COMPOUNDS

[75] Inventor: David C. Peterson, Portage, Mich.

[73] Assignees: The Upjohn Company, Kalamazoo, Mich.

[21] Appl. No.: 809,254

[22] Filed: Jun. 23, 1977

Related U.S. Application Data

[62] Division of Ser. No. 614,244, Sep. 17, 1975.

[51] Int. Cl.² .................... C07C 69/76; C07C 177/00
[52] U.S. Cl. ................................ 560/53; 260/520 C; 260/520 R
[58] Field of Search ...................... 260/520 R, 520 C; 560/53

[56] References Cited

U.S. PATENT DOCUMENTS 4,066,836  1/1978  Morton, Jr. ............................ 560/53

FOREIGN PATENT DOCUMENTS 6,908,506  8/1969  Netherlands Antilles ................ 560/53

OTHER PUBLICATIONS

Derwent Abstr. 246804/14 NL. 7610-184 (21-03-77).

*Primary Examiner*—Paul J. Killos
*Attorney, Agent, or Firm*—Robert A. Armitage; Robert A. Armitage, et al

[57] ABSTRACT

Prostaglandin analogs with the following cyclopentane ring structure:

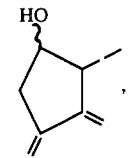

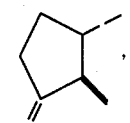

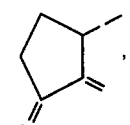

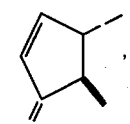

or

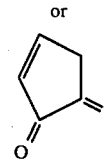

are disclosed along with intermediates useful in their preparation and processes for their preparation. These analogs are useful for some of the same pharmacological purposes as the prostaglandins, particularly and especially as blood platelet aggregation inhibitors.

25 Claims, No Drawings

3,7-INTER-M-PHENYLENE-4,5,6-TRINOR-PGD$_1$ COMPOUNDS

The present application is a divisional application of Ser. No. 614,244, filed Sept. 17, 1975, now pending issuance as a United States Patent.

The present invention relates to prostaglandin analogs, for which the essential material constituting disclosure therefor is incorporated by reference here from Serial No. 809,248, filed June 23, 1977, which is a divisional application of Ser. No. 614,244.

I claim:

1. A prostaglandin analog of the formula

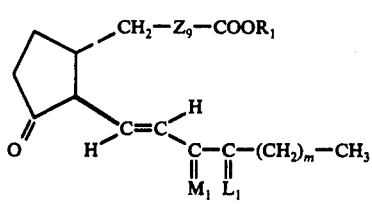

wherein m is one to 5, inclusive;
wherein M$_1$ is

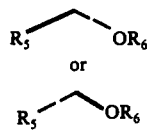

wherein R$_5$ and R$_6$ are hydrogen or methyl, with the proviso that one of R$_5$ and R$_6$ is methyl only when the other is hydrogen;
wherein L$_1$ is

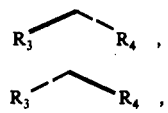

or a mixture of

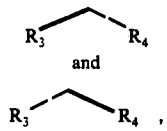

wherein R$_3$ and R$_4$ are hydrogen, methyl, or fluoro, being the same or different, with the provisio that one of R$_3$ and R$_4$ is fluoro only when the other is hydrogen or fluoro;
wherein R$_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation; and
wherein Z$_9$ is

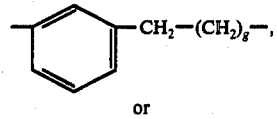

or

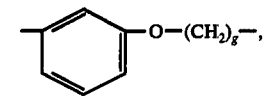

wherein g is one, 2, or 3.

2. A compound according to claim 1, wherein M$_1$ is

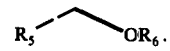

3. A compound according to claim 1, wherein M$_1$ is

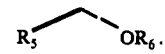

4. A compound according to claim 3, wherein m is 3.

5. A compound according to claim 4, wherein Z$_9$ is

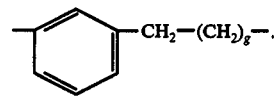

6. A compound according to claim 5, wherein g is 3.

7. A compound according to claim 5, wherein g is one.

8. A compound according to claim 7, wherein R$_5$ and R$_6$ are both hydrogen.

9. A compound according to claim 8, wherein R$_3$ and R$_4$ are both hydrogen.

10. 3,7-Inter-m-phenylene-4,5,6-trinor-9-deoxy-PGD$_1$, a compound according to claim 9.

11. A compound according to claim 8, wherein R$_3$ and R$_4$ are both fluoro.

12. 16,16-Difluoro-3,7-inter-m-phenylene-4,5,6-trinor-9-deoxy-PGD$_1$, a compound according to claim 11.

13. A compound according to claim 5, wherein Z$_9$ is

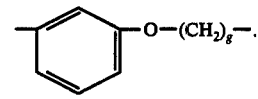

14. A compound according to claim 13, wherein g is 3.

15. A compound according to claim 14, wherein R$_5$ and R$_6$ are both hydrogen.

16. A compound according to claim 15, wherein R$_3$ and R$_4$ are both hydrogen.

17. 2a,2b-Dihomo-3,7-inter-m-phenylene-4,5,6-trinor-3-oxa-9-deoxy-PGD$_1$, a compound according to claim 16.

18. A compound according to claim 15, wherein R$_3$ and R$_4$ are both fluoro.

19. 2a,2b-Dihomo-16,16-difluoro-3,7-inter-m-phenylene-4,5,6-trinor-3-oxa-9-deoxy-PGD$_1$, a compound according to claim 18.

20. A compound according to claim 13, wherein $g$ is one.

21. A compound according to claim 20, wherein $R_5$ and $R_6$ are both hydrogen.

22. A compound according to claim 21, wherein $R_3$ and $R_4$ are both hydrogen.

23. 3,7-Inter-m-phenylene-4,5,6-trinor-3-oxa-9-deoxy-PGD$_1$, a compound according to claim 22.

24. A compound according to claim 21, wherein $R_3$ and $R_4$ are both fluoro.

25. 16,16-Difluoro-3,7-inter-m-phenylene-4,5,6-trinor-3-oxa-9-deoxy-PGD$_1$, a compound according to claim 24.

* * * * *

UNITED STATES PATENT OFFICE
CERTIFICATE OF CORRECTION

Patent No. 4,118,591                    Dated October 3, 1978

Inventor(s)  David C. Peterson

It is certified that error appears in the above-identified patent and that said Letters Patent are hereby corrected as shown below:

Column 1, line 13, "filed June 23, 1977," should read -- filed June 23, 1977, now U.S. Patent 4,099,014, --.

Signed and Sealed this

Thirteenth Day of March 1979

[SEAL]

Attest:

RUTH C. MASON
Attesting Officer

DONALD W. BANNER
Commissioner of Patents and Trademarks